United States Patent [19]

Chiang

[11] Patent Number: 4,945,062
[45] Date of Patent: Jul. 31, 1990

[54] CONTROL FOR BLOOD GAS/CALCIUM ANALYSIS INSTRUMENTATION

[75] Inventor: Ching Chiang, Acton, Mass.

[73] Assignee: Bionostics Incorporated, Acton, Mass.

[21] Appl. No.: 207,182

[22] Filed: Jun. 15, 1988

[51] Int. Cl.$^5$ ............................................. G01N 31/00
[52] U.S. Cl. ....................................... 436/11; 436/15; 436/18; 436/19; 252/408.1
[58] Field of Search ........................................ 436/8–18, 436/74, 79, 19, 66, 68; 252/408.1; 73/1 R, 1 G

[56] References Cited

U.S. PATENT DOCUMENTS

| | | | |
|---|---|---|---|
| 4,163,734 | 8/1979 | Sorensen et al. | 436/11 |
| 4,279,775 | 7/1981 | Louderback et al. | 436/11 |
| 4,299,728 | 11/1981 | Cormier et al. | 436/11 |
| 4,363,633 | 12/1982 | Christiansen | 436/19 |
| 4,369,127 | 1/1983 | Cormier et al. | 436/11 |
| 4,403,038 | 9/1983 | Asakura et al. | 436/16 |
| 4,469,792 | 9/1984 | Simmonds et al. | 436/11 |
| 4,753,888 | 6/1988 | Chiang | 436/11 |
| 4,806,486 | 2/1989 | Sprokholt et al. | 436/19 |
| 4,871,678 | 10/1989 | Wahl et al. | 436/19 |

OTHER PUBLICATIONS

Ramieri, Jr. et al., "New Method for Rapid Determination of Carboxyhemoglobin by Use of Double-Wavelength Spectrophotometry", *Clin. Chem.*, 20/2:278–281 (1974).
Siggaard-Andersen et al., "Hemoglobin Pigments, Spectrophotometric Determination of Oxy-, Carboxy-, Met, and Sulfhemoglobin in Capillary Blood", *Clin. Chim. Acta.*, 42:85–100 (1972).
Zwart et al., "Determination of Hemoglobin Derivatives with the IL282 CO-Oximeter as Compared with a Manual Spectrophotometric Five-Wavelength Method", *Clin. Chem.*, 27711:1903–1907 (1981).
Zwart et al., "A Multi-Wavelength Spectrophotometric Method for the Simultaneous Determination of Five Haemoglobin Derivatives", *J. Clin. Chem. Clin. Biochem.*, 19:457–463 (1981).
Ringbom, *Complexation in Analytical Chemistry*, Interscience Publishers, (New York: 1963), pp. 25–67.
Perrin et al., *Buffers for pH and Metal Ion Control*, Chapman and Hall, (New York: 1974), pp. 94–108.
Chaberek et al., *Organic Sequestering Agents* (1959).
Ferguson et al., "Hydrogen Ion Buffers for Biological Research", *Analyt. Biochem.*, 104:300–310 (1980).
Good et al., "Hydrogen Ion Buffers for Biological Research", *Biochem.*, 5: No. 2, 467–477 (1966).

*Primary Examiner*—Christine M. Nucker
*Assistant Examiner*—T. J. Wallen
*Attorney, Agent, or Firm*—Hamilton, Brook, Smith & Reynolds

[57] ABSTRACT

A liquid control standard for the use in the qualilty assurance of blood analysis instrumentation systems is disclosed. The liquid control standard is able to act as a control standard for blood gas instrumentation systems measuring pH, $pCO_2$ and $pO_2$ of blood, as a liquid control standard for ion selective electrode instrumentation systems for the measuring of electrolytes such as ionized calcium and total calcium as well as Na, K and Li ions in the blood and, optionally, as a control standard for a co-oximeter measuring the amount of total hemoglobin present in the blood and the relative amounts of other hemoglobin fractions present in the blood.

17 Claims, No Drawings

CONTROL FOR BLOOD GAS/CALCIUM ANALYSIS INSTRUMENTATION

BACKGROUND OF THE INVENTION

The measurement of total calcium in blood has been used in the clinical practice for many years for routine diagnosis by physicians.

During the past several years, the measurement of ionized calcium ($Ca^{++}$, free calcium ions) has been recommended to provide an indicator which is more effective than total calcium in cases such as hyperparathyroidism, pancreatitis, renal diseases, and hypocalcemia resulting from repeated blood transfusion, malignancy, and other causes. Furthermore, it is also thought that the simultaneous measurement of both total and ionized calcium is beneficial in the clarification of certain diagnosis. For example, in some clinical cases of multiple myeloma in which hypercalcemia becomes a severe complication, the total calcium in patients is highly elevated while their ionized calcium is normal. Therefore both total and ionized calcium measurements are needed to provide information for a proper diagnosis.

Various instrumentation systems have been developed for the determination of both total and ionized calcium. In the recent past, these instruments have utilized ion-selective-electrodes (ISE) for calcium and other electrolyte measurements. In addition, there has been the development of blood gas analyzers to which electrolyte analysis capabilities have been included through the integration of ion selective electrodes with electrodes for measurement of pH, $pCO_2$ and $pO_2$. Furthermore, the capability for measuring a variety of other parameters (e.g., total hemoglobin, hematocrit, glucose) has also been included in some of these instruments.

It is common practice to employ a control solution for verifying the accuracy and reliability of diagnostic instrumentation systems. When analyzed by the instrumentation for which they are intended, these control solutions should closely mimic actual patient samples for both normal and abnormal conditions.

For instrumentation systems which measure both blood gas and ionized calcium along with other electrolytes (such as Na, K, Li and Cl), a single control solution is needed. To date, this has been accomplished in aqueous solutions by incorporating soluble salts of the desired electrolytes into the buffered aqueous solution which has been tonometered with carbon dioxide and oxygen to provide the pH, $pCO_2$ and $pO_2$ control values needed for quality control of blood gas analyzers.

Using soluble calcium salts in such a solution, it is very difficult to stabilize the calcium ions in the solution in a satisfactory manner. This is because of the tendency of free ionic calcium to combine with anions and precipitate out of solution. Also, soluble calcium salts are completely ionized and only a small portion of the ionized calcium ion is bound if anions such as phosphate, sulfate, bicarbonate, organic acid buffers or combinations of these are present in the same solution. This results in a low binding of calcium, typically less than 15% of the total calcium, with more than 85% of the calcium in ionized form.

A solution for the quality control of calcium of this nature can provide control values for ionized calcium, but does not provide an effective range of total calcium values to simulate the dynamic range of patient samples.

SUMMARY OF THE INVENTION

This invention relates to autoclavable, stable, homogeneous liquid control solutions which provide measuring parameters for instrumentation systems which analyze, in blood samples, pH, $pCO_2$ and $pO_2$ and total and ionized calcium for ISE measurements. Further, the invention can include control parameters for additional electrolytes (e.g. Na, K, Cl, Li), other blood components (e.g. glucose, BUN) and dyes to provide colormetric determinations of hemoglobin.

The liquid control is comprised of an aqueous solution buffered to a pH of about 7.1 to about 7.7 and containing sufficient bicarbonate ion to provide a $pCO_2$ of from about 15 mmHg to about 80 mmHg after subsequent equilibration with the desired levels of gaseous carbon dioxide, gaseous oxygen to provide a $pO_2$ of from about 50 mmHg to about 400 mmHg, salts of calcium and a calcium sequestering agent to provide ionized calcium and total calcium concentrations in a predetermined range and optionally, other soluble constituents (e.g. salts, dyes and other soluble blood components) to provide various control parameters useful in a blood gas/calcium control material.

DETAILED DESCRIPTION OF THE INVENTION

The invention is an autoclavable, stable, homogeneous liquid control standard comprised of an aqueous solution buffered to a pH of from about 7.1 to about 7.7 and containing sufficient bicarbonate ion to provide a $pCO_2$ of from about 15 mmHg to about 80 mmHg after subsequently equilibrated with the desired levels of gaseous carbon dioxide, gaseous oxygen to provide a $pO_2$ of from about 50 mmHg to about 400 mmHg; a calcium source to provide a total calcium concentration in a predetermined range; a calcium sequestering agent to provide an ionized calcium concentration in a predetermined range; sodium, potassium and lithium salts in physiological amounts to provide measurements of these ions in solution; optionally, absorbance means to provide measurements of total hemoglobin and of several hemoglobin fractions; and optionally, glucose to provide physiological values.

In the preferred embodiment of the invention, the ionized calcium concentration is between about 0.5 mM and about 1.7 mM, the total calcium concentration is between about 1.3 mM and about 3.6 mM, and the ratio of the ionized calcium concentration to the total calcium concentration is between about 30% and about 60%.

In order to provide the desired pH for the respective normal, acidosis or alkalosis conditions, a buffer material should be selected which has a $pK_a$ close to the desired working pH. A particularly useful buffer material for providing the desired pH conditions in the control solution of this invention is N-2-hydroxyethylpiperazine-N'-2-ethanesulfonic acid (HEPES) which has a $pK_a$ of 7.31 at 37° C. Other suitable buffer materials are, for example, N-tris-(hydroxymethyl)methyl-2-aminoethanesulfonic acid (TES), which has a $pK_a$ of 7.16 at 37° C.; 3-(N-morpholino) propanesulfonic acid (MOPS), which has a $pK_a$ of 7.01 at 37° C.; Tris-(Hydroxymethyl) aminomethane (TRIS) which has a $pK_a$ of 7.77 at 37° C.; N-Tris (hydroxymethyl)methyl glycine (TRICINE), which has a $pK_a$ of 7.79 at 37° C.; and N,N-Bis (2hydroxyethyl) glycine (BICINE), which has a $pK_a$ of 8.04 at 37° C. These and other such suitable buffer materials, including the sodium salt derivatives, are described by Good et al. *Biochemistry* 5, 467-77 (1966) and Ferguson et al., *Analytical Biochemistry* 104, 300-310 (1980), the teachings of which are hereby incorporated by reference.

The desired $pCO_2$ level is provided in part by addition of bicarbonate ion, for example, $NaHCO_3$, to the aqueous solution that a $pCO_2$ of from about 15 mmHg to about 80 mmHg is reached after subsequently being equilibrated with the desired levels of gaseous carbon dioxide. The desired $pO_2$ level of from about 50 mmHg to about 400 mmHg is facilitated by addition of gaseous oxygen to the solution or the head space in the receptacle containing the aqueous solution. Addition of gaseous carbon dioxide similarly can facilitate maintenance of the aforesaid desired $pCO_2$ levels.

In order to provide physiological electrolyte levels for testing ISE electrolyte instruments, it is necessary to dissolve a variety of salts of the desired electrolytes into the control standard solution. Typical electrolyte analysis instruments measure levels of chloride, sodium, potassium, lithium and calcium present in solution. Therefore, controls having a physiological range of electrolyte values of Cl, Na, K, Li and Ca can be made by the addition of appropriate quantities of chloride, sodium, potassium, lithium and calcium salts such as NaCl, KCl, LiCl and $CaCl_2$.

In earlier control standards, it has been difficult to maintain ionized calcium ($Ca^{++}$) in solution containing a dynamic range of total calcium especially when tonometrically equilibriated with gaseous carbon dioxide. This is due to the interaction between the dissolved, ionized calcium and dissolved carbon dioxide in solution which leads to the formation of calcium carbonate which precipitates out of solution. This effect does not generally occur in blood serum because albumin present in the serum acts as a complexing ligand to form a reversibly dissociable calcium complex. The complex acts as a buffering agent to maintain the calcium ion concentration within a certain range.

Unfortunately, the presence of albumin in a synthetic control standard produces a standard with properties that are less than satisfactory. Since albumin is a biological product, solutions containing it are perishable, even if refrigerated. Additionally, although albumin can be pasteurized, it becomes denatured if it is subjected to storage at temperatures greater than the range of about 2° C. to about 8° C. Furthermore, solutions containing albumin generally cannot survive sterilization in an autoclave. Such treatment denatures the albumin and renders the solution unusable. The requirement for refrigerated storage, the limited shelf-life and the inability to be sterilized via autoclave exhibited by albumin-containing control standards add both expense and inconvenience to their use.

Calcium complexation which avoids the disadvantages of albumin is provided in this invention by a calcium complexing agent which is any of a variety of chelating or sequestering agents. Representative calcium complexing agents are organic acids such as alpha-amino acids, alpha-hydroxy acids, dicarboxylic acids, polycarboxylic acids and derivatives thereof. Additionally, some inorganic acids such as sulfuric acid, phosphoric acid and polyphosphoric acid can be used to stabilize the free calcium ion concentration in solution.

The control standards of the type described herein are highly stable. For example, they can retain their properties for at least two years under normal handling and storage at room temperature. Thus, the need to refrigerate the control standards has been eliminated. Additionally, the control standards of the type described herein can survive sterilization in an autoclave, thereby offering additional advantages over albumin-containing control standards.

These chelating or sequestering agents, when present in solution, form ligands which complex with the calcium ions. When the ligand is present in the solution, a given amount of the calcium ions is bound, thereby forming reversibly dissociable complexes, and the free calcium ion is buffered at a desired concentration in the presence of excess total calcium ions in a manner analagous to hydrogen ions in the the pH buffers. Proper selection of the calcium buffer system serves to maintain a relatively stable free calcium ion concentration in virtually any desired range, including, but not limited to, the physiological range. For example, among the organic acid calcium binding ligands, some, such as ethylene-diaminetetraacetic acid (EDTA), have very strong calcium binding capacity. The calcium binding capacity can be quantified by a calcium complexing constant (log $K_{Ca}$) which, in the case of EDTA is about 10.6 at 25° C. and I=0.15, where I represents the ionic strength of the solution. Thus, most of the calcium ions in solution become tightly bound to the EDTA leaving a free calcium ion concentration in solution too low to be measured by ISE instruments.

In contrast, ligands having low calcium complexing constants require large amounts to be present in solution to provide a calcium ion concentration in the standard that approximates a value in the dynamic range of physiological concentration. Otherwise, very little $Ca^{++}$ will bind to the ligand, thereby leaving a large amount of $Ca^{++}$ to bind with the $CO_2$ in solution causing a great variation of $CA^{++}$ value in the solution when subdivided into individual containers. One example of a sequestering agent with a calcium complexing constant which may be too low to be effective is glutamic acid, having a log $K_{Ca}$ of about 1.6 at 25° C. and I=0.15.

Therefore, for the purposes of utilization in this invention, the calcium complexing ligand should be one having a calcium complexing constant between about 1.5 and about 8 and preferably between about 2 and about 6 at physiological temperature and pH ranges.

A variety of complexing ligands for the calcium ion can be found with different basic structures giving a wide range of complexing constants. However, most of these compounds are the derivatives of a few basic structures such as alpha-amino acids, alpha-hydroxy acids, dicarboxylic and polycarboxylic acids. Illustrative compound groups are presented below. Among these groups, the derivatives of ethylene-diaminetetraacetic acid have very high value of log $K_{(CA)}$; but in compounds in which a central alkylene group is extended to greater than two methylenes or in which the molecules of acetic acids are substituted by other acids, the value of log $K_{(Ca)}$ is reduced for suitable use.

CALCIUM COMPLEXING LIGANDS (A) Iminodicarboxylic acid

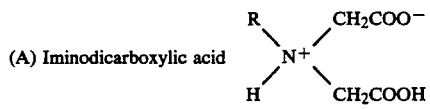

| | Compound | R | Complex | Log $K_{(Ca)}$ |
|---|---|---|---|---|
| Examples: | imino-diacetic acid | —H | Ca (L) | 2.6 |
| | N-methyliminodiacetic acid | —CH$_3$ | Ca (L) | 3.7 |
| | 2-sulfanilindiacetic acid | (2-HO$_3$S-phenyl) | Ca (L) | 4.6 |
| | 2-aminobenzoic acid, N,N-diacetic acid | (2-HOOC-phenyl) | Ca (L) | 5.1 |
| | N-(2-acetamido)imino diacetic acid | —CH$_2$CNH$_2$ | Ca (L) | 4.0 |
| | N-cyanomethyliminodiacetic acid | —CH$_2$CN | Ca (L) | 2.7 |
| | N-methoxyethyliminodiacetic acid | —CH$_2$CH$_2$OCH$_3$ | Ca (L) | 4.5 |
| | aminobarbituric acid, N,N-diacetic acid | (barbituric ring) | Ca (L)$_2$ | 5.2 |
| | N-hydroxyethyliminodiacetic acid | —CH$_2$CH$_2$OH | Ca (L) | 4.6 |
| | N-carbethoxy-beta-iminoethyl-iminodiacetic acid | —CH$_2$CH$_2$-N(COC$_2$H$_5$) | Ca (L) | 3.0 |
| | beta-mercaptoethyliminodiacetic acid | —CH$_2$CH$_2$SH | Ca (L) | 4.9 |
| | beta-aminoethylsulfonic acid-N,N-diacetic acid | —CH$_2$CH$_2$SO$_3$ | Ca (L) | 4.1 |
| | aminoethylphosphoric acid-N,N-diacetic acid | —CH$_2$CH$_2$PO(OH)$_2$ | Ca (L) | 5.4 |
| | ethylenediamine-N,N-diacetic acid | —CH$_2$CH$^+_2$NH$_2$ | Ca (L) | 4.6 |

(B) Iminotricarboxylic acid

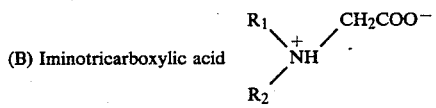

| | Compound | $R_1$ | $R_2$ | Complex | log $K_{(Ca)}$ |
|---|---|---|---|---|---|
| Examples: | nitrilotriacetic acid | —CH$_2$COOH | —CH$_2$COOH | Ca (L) | 6.4 |
| | nitrilopropionic diacetic acid | —CH$_2$COOH | —CH$_2$CH$_2$COOH | Ca (L) | 5.0 |

(C) Ethylenediaminediacetic acid

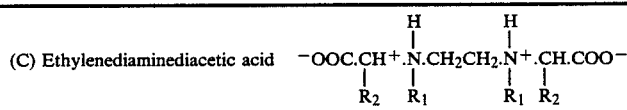

| | Compound | $R_1$ | $R_2$ | Complex | log $K_{(Ca)}$ |
|---|---|---|---|---|---|
| Examples: | N,N'-dihydroxyethyl-ethylenediaminediacetic acid | —CH$_2$CH$_2$OH | —H | Ca(OH)$_2$(L) | 5.7 |
| | N,N'-ethylene-bis-[2-(0-hydroxyphenyl)]glycine | —H | 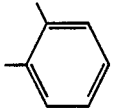 | CaH (L) | 4.8 |

-continued

CALCIUM COMPLEXING LIGANDS (D) Ethylenediaminetriacetic acid $$^{-}OOCCH_2\overset{H}{\underset{R}{\overset{|}{N^+}}}.CH_2CH_2\overset{H}{\underset{CH_2COOH}{\overset{|}{N^+}}}.CH_2COO^{-}$$

| | Compound | R | Complex | log $K_{(Ca)}$ |
|---|---|---|---|---|
| Examples: | N-benzylethylethylenediamine-triacetic acid | —CH$_2$.CH$_2$—⟨phenyl⟩ | Ca (L) | 6.7 |
| | N-hydroxyethylethylenediamine-triacetic acid | —CH$_2$CH$_2$OH | Ca (L) | 8.0 |

(E) Alkylenediaminetetraacetic acid $$\begin{array}{c}^{-}OOCCH_2\\ HOOCCH_2\end{array}\!\!\!N^+.(R).N^+\!\!\!\begin{array}{c}CH_2COO^{-}\\ CH_2COOH\end{array}$$

| | Compound | R | Complex | log $K_{(Ca)}$ |
|---|---|---|---|---|
| Examples: | trimthylenedisminetetraacetic acid | —CH$_2$CH$_2$CH$_2$— | CaH(L) | 3.1 |
| | tetramethylenediaminetetraacetic acid | —CH$_2$CH$_2$CH$_2$CH$_2$— | Ca (L) | 5.0 |
| | 1,3-diaminocyclohexane-N,N'-tetraacetic acid | ⟨cyclohexyl⟩ | Ca (L) | 4.8 |
| | 1,4-diaminocyclohexane-N,N'-tetraacetic acid | ⟨cyclohexyl⟩ | Ca (L) | 4.2 |

(F) Other Groups

| | Compound | Complex | log $K_{(Ca)}$ |
|---|---|---|---|
| | a. alpha-hydroxydicarboxylic acid | | |
| Example: | tartaric acid | Ca(OH)$_2$L | 2.2 |
| | b. tricarboxylic acid | | |
| Example: | citric acid | Ca(OH)L | 3.2 |
| | c. hydroxybenzene sulfonic acid | | |
| Examples: | 1,2-dihydroxybenzene-3,5-disulfonic acid | Ca(O)$_2$L | 5.8 |
| | 8-hydroxyquinoline-5-sulfonic acid | Ca (L) | 4.8 |
| | d. polyphosphoric acid | | |
| Examples: | triphosphoric acid | Ca (L) | 5.0 |
| | trimetaphosphoric acid | Ca (L) | 3.5 |
| | tetrametaphosphoric acid | Ca (L) | 4.9 |
| | adenosine diphosphate | Ca (L) | 2.8 |
| | adenosine triphosphate | Ca (L) | 3.6 |
| | e. diethylenetriaminetetraacetic acid | | |
| Example: | N-hydroxyethyl-N',N''-diethylenediamine-tetraacetic acid | CaH(L) | 5.2 |
| | f. ethylenediaminetetra(phosphoric) acid | | |
| Example: | ethylenediamine-tetra(methylenephosphoric-acid) | Ca (L) | 6.1 |

In a preferred embodiment of the invention, the sequestering agent is used in solution with calcium ions to provide an ionized calcium concentration in a range approximating the dynamic range of between about 0.5 mM and about 1.7 mM in the presence of a total calcium concentration ranging between about 1.3 mM and about 3.6 mM, wherein the concentration ratio of ionized calcium to total calcium is in the range of about 30% to about 60%. Additionally, when used in a control standard for pH/blood gas instruments, the sequestering agents above do not alter the pH/blood gas properties of the standard. In certain cases, however, in which the control standard contains certain dyes to simulate hemoglobin content for co-oximetry measurements, a reaction between one of a number of the calcium sequestering agents and certain dyes can reduce the pO$_2$ of the control standard after storage for a period of 1 to 10 weeks at temperatures at or above about 37° C. This problem can be avoided by selecting calcium complexing agents which are not reactive with the dyes, such as one of the polycarboxylic acids. Alternately, the problem is avoided by limiting the use of the standard to pH/blood gas and ISE electrolytes instrumentation, thereby eliminating the need for dyes.

In the most preferred embodiment of the invention, the calcium sequestering agent comprises citric acid, (HOOCCH$_2$C(OH)(COOH)CH$_2$COOH). Citric acid is preferred because it has an appropriate complexation constant with calcium, ($K_{Ca}=3.22$ at 25° C. and $I=0.15$), and because it does not react with dyes to reduce the $pO_2$ of the control solution. Thus, a control standard containing citric acid as the calcium sequestering agent can be used in a control standard useful for pH/blood gas analysis, ISE electrolytes analysis (including free calcium ions) and co-oximetric analysis. Additionally, citric acid is preferred because of its low cost, ready availability and ease and safety in storage and handling.

The optional use of the multiple control standard for co-oximetry will now be described. In a typical co-oximeter, a whole blood sample is aspirated into the instrument, mixed with diluent, hemolyzed, and brought to a constant temperature in a cuvette. A microcomputer calculates the total hemoglobin concentration present, expressed in grams per one hundred milliliters of whole blood g/dL THb. A typical co-oximeter also measures the percent oxyhemoglobin ($O_2Hb$), carboxyhemoglobin (COHb), methemoglobin (MetHb), and reduced hemoglobin. Each of these species of hemoglobin will absorb light at different wavelengths along the 500–650 nm range.

The control solution of the present invention contains absorbance means, such as dyes, which can absorb light in the 500–650 nm range at approximately the same percentage and wavelength as predetermined concentrations of the different hemoglobin species. By using this control solution with the co-oximeter, it can be determined whether or not the co-oximeter is functioning properly and whether or not the instrument needs to be recalibrated.

The absorbance means need not absorb light exactly as the different species of hemoglobin do. What is important is that a relationship can be determined such that the light absorbed by the absorbance means in the control solution can be correlated to a specific absorbance level of the particular hemoglobin species in question.

In a preferred embodiment, the control solution of the present invention contains a combination of Acid Red Dye #27 (CI 16185), Acid Yellow Dye #23 (CI 19140) and Acid Blue Dye #9 (CI 42090). Also used is the combination of Ponceau 3R Red Dye (CI 16155) and Acid Blue Dye (CI 42090).

The blue dye is used because it has a maximum absorbance of light at 630 nm as does methemoglobin.

The red dyes were chosen due to the fact that they show absorbance levels at the 560 nm and 535 nm wavelengths as does oxyhemoglobin, at the 570 nm wavelength as does carboxyhemoglobin, and at the 550 nm wavelength as does reduced hemoglobin. By altering the concentrations of these dyes in the control solution, the control solution can simulate samples of blood having various levels of the different fractions of hemoglobin and of total hemoglobin.

In a preferred embodiment of this invention, a combination of the salts of the acid dyes as well as the addition of NaOH, NaCl, $NaN_3$ and $NaHCO_3$ can be used to provide a physiological Na concentration for ISE electrolytes instrumentation.

The density of the control solution can be placed at 1.01 to 1.03 and the viscosity of the solution from 2 to 4 centipoises which are similar to the density and viscosity of blood by adding up to 70 g/L of natural polymers, such as bovine serum albumin, or one of the synthetic polymers such as Polyethylene glycol (PEG) 8000, Polyvinylpyrrolidone (PVP) 40, Polyvinyl alcohol (PVA) and Ficoll 400. (Ficoll 400 is a synthetic high polymer made by the copolymerization of sucrose and epichlorohydrin produced by the Pharmacia Fine Chemicals AB Company of Uppsala, Sweden. Ficoll 400 indicates that the polymer has a molecular weight of approximately 400,000.)

To ensure a stable product which, under normal handling and storage will retain its properties for more than two years at room temperature, a chemical preservative such as formaldehyde can be added to the solution. Alternately, the solution can be sterilized by either membrane filtration or by high temperature sterilization in an autoclave if the solution does not contain the polymers used to increase the viscosity of the solution.

A preferred formulation is listed below. By varying the concentrations of the reagents in the following formulation, a varied number of control standards can be produced. These control standards will then have different levels of pH, $pCO_2$, $pO_2$; different concentrations of chloride, sodium, potassium, lithium and calcium ions as well as total calcium; and different simulations of total hemoglobin fractions. For example, the formulation listed below contains chlorine, calcium, sodium and potassium salts as the electrolyte, however, other formulations can include various combinations of some or all of the previously described electrolyte compositions.

| Formulation I | |
| --- | --- |
| Compound | Concentration |
| HEPES and/or TRIS, MOPS | 20 to 100 mM |
| NaCl | 40 to 100 |
| KCl | 2 to 8 |
| LiCl | 0.3 to 3 |
| NaOH | 0 to 60 |
| $CaCl_2$ | 1.3 to 3.6 |
| Citric Acid | 1.0 to 2.5 |
| $NaHCO_3$ | 18 to 26 |
| Acid Red Dye #27 (CI 16185) | 2 to 5 |
| Acid Yellow Dye #23 (CI 19140) | 3 to 7 |
| Acid Blue Dye #9 (CI 42090) | 0.015 to 0.08 |
| Polymer (PVA, Ficoll 400, PEG 8000, PVP 40 or Lovine serum albumin) | 0 to 50 g/l |

Using varying amounts of the reagents from the preferred formulations, three levels of multiple control standards can be formulated, namely Level I Control, Level II Control and Level III Control.

The multiple control standard of Level II simulates normal blood having a pH of about 7.4, a $pCO_2$ of about 40 mmHg and $pO_2$ of about 100 mmHg.

The multiple control standard of Level II contains a sufficient concentration of dye to simulate a total hemoglobin concentration of about 14 g/100 ml of blood. This total hemoglobin reading can be produced by placing red dye, yellow dye and blue dye into solution to give the control standard the ability to absorb the light spectrum in the wavelengths between 400 to 650 nm. The yellow dye is used in order to give the control the appearance of blood but does not absorb light in the critical ranges. A preferred concentration of dyes is about 3.5 mM of Acid Red Dye #27 (CI 16185), about 5 mM of Acid Yellow Dye #23 (CI 19140) and about 0.04 mM of Acid Blue Dye #9 (CI 42090). This concentration of dyes in solution results in a control standard having an appearance of blood and giving a total hemoglobin reading of about 14 grams in 100 ml of aqueous solution as measured by the Corning 2500 Co-oximeter, 9 g/100 ml by the IL282 Co-oximeter and 26 g/100 ml by the ABL-30 Blood Gas Analyser. The multiple control standard of Level II also contains a concentration of sodium ions of about 140 mM, a concentration of potassium ions of about 5 mM, a concentration of lithium ions of about 1.1 mM, a concentration of ionized calcium of about 1.1 mM and a concentration of total calcium of about 2.5 mM.

The multiple control standard of Level I simulates blood having a low pH of about 7.10 to about 7.20, a high $pCO_2$ of from about 60 mmHg to about 70 mmHg, and a low $pO_2$ of from about 50 mmHg to about 65 mmHg. (This control standard thus simulates acidosis.) The control standard of Level I also contains a low concentration of Na ions from about 115 mM to about 125 mM, a low concentration of K ions from about 2.5 mM to about 3.5 mM, a low concentration of Li ions from about 0.3 mM to about 0.6 mM, a high concentration of ionized calcium of about 1.5 mM to about 1.7 mM and a high concentration of total calcium of about 3.3 mM to about 3.6 mM.

The multiple control standard of Level I also contains a lower concentration of all dyes to simulate a total hemoglobin of about 9 g/100 ml of blood as read by the Corning 2500 Co-oximeter. A preferred control solution of Level I contains about 2 mM of Acid Red Dye #27 (CI 16185), about 3 mM of Yellow Dye #23 (CI 19140), and about 0.015 mM of Acid Blue Dye #9 (CI 42090).

The multiple control standard of Level III simulates a sample of blood having a high pH of about 7.6, a low $pCO_2$ of about 22 mmHg and a high $pO_2$ level of about 150 mmHg. (This control standard thus simulates alkalosis). The multiple control standard of Level III also contains a sufficient concentration of dyes to simulate a high total hemoglobin of about 18 g/100 ml of solution. This total hemoglobin reading is produced by having a higher concentration of all dyes, preferably about 5 mM of Acid Red Dye #27 (CI 16185), about 7 mM of Acid Yellow Dye #23 (CI 19149), and about 0.08 mM of Acid Blue Dye #9 (CI 42090). The control standard of Level III also contains a higher concentration of sodium ions of about 160 mM and of potassium ions of about 7 mM, a concentration of lithium ions of about 2.6 mM, a concentration of ionized calcium of about 0.6 mM and a concentration of total calcium of about 1.7 mM.

The desired $pCO_2$ value is provided in part by the addition of bicarbonate ion, e.g. $NaHCO_3$ to the aqueous solution. $CO_2$ gas is then added to the aqueous solution until a $pCO_2$ of from about 15 mmHg to about 80 mmHg is attained, depending upon which control level is being produced.

The desired $pO_2$ level of from about 50 mmHg to about 160 mmHg, depending upon which control level is being produced, is reached by the addition of gaseous oxygen to the solution and head space in the receptacle containing the aqueous solution. Addition of gaseous carbon dioxide similarly can facilitate maintenance of the aforesaid desired $pCO_2$ levels.

The final control standard solution is retained in a sealed or air-tight receptacle such as, for example, a glass vial or ampule to retain the desired gas equilibrium. The head space in the receptacle can be filled with an appropriate gas to facilitate the provision of the aforesaid $pCO_2$ conditions. For example, for the acidosis blood gas control, a mixture of 6.5% oxygen, 5.9% of carbon dioxide and 87.6% of nitrogen is used. For the normal blood gas control a mixture of about 4.1% of carbon dioxide, 11.8% of oxygen and 84.1% of nitrogen is used. For the alkalosis blood gas control a mixture of about 2.3% of carbon dioxide, 18% of oxygen and 79.7% of nitrogen is used. It will be appreciated that any other inert gas can be used as a substitute for part or all of the nitrogen portion of the head space in the foregoing illustrative examples.

Another embodiment of the invention can have the following formulation:

| FORMULATION II | |
|---|---|
| COMPOUND | CONCENTRATION |
| HEPES | 20 to 100 mM |
| NaCl | 40 to 100 |
| KCl | 2 to 8 |
| LiCl | 0.3 to 3 |
| $CaCl_2$ | 1.3 to 3.6 |
| N-hydroxyethyl-iminodiacetic acid | 1.0 to 2.5 |

In this embodiment, the citric acid of Formulation I has been replaced by N-hydroxyethyl iminodiacetic acid. It must be pointed out, however that any of the previously described sequestering agents can be substituted into the above formulation to replace the citric acid.

The color dyes used in Formulation I were not added to Formulation II. Thus, Formulation II has no hemoglobin control value. This formulation is suited for use with instruments measuring pH/blood gas and electrolytes.

In yet another preferred embodiment, the sequestering agent has been selected from the group consisting of tartaric acid, nitriloacetic acid (NTA), N-(2-acetamido)imino-diacetic acid (ADA), and N,N-bis(2-hydroxyethyl) glycine. These sequestering agents are used in an amount which allows the concentration of ionized calcium in solution to be maintained in the range of about 0.5 mM to about 1.7 mM and the total calcium concentration in solution to be maintained in the range of about 1.3 mM to about 3.6 mM. It must be pointed out, however, that while these are preferred sequestering agents, the invention is not intended to be limited as such. Rather, the invention is intended to encompass the class of sequestering agents described in the table of Calcium Complexing Ligands.

The following specific and detailed examples will further illustrate the invention although it will be appreciated that these examples are not meant to restrict the invention to the specific details found in each example.

EXAMPLE 1

The blood gas control liquids are preferably formulated to represent three levels of pH, $pCO_2$ and $pO_2$ values, to represent three levels of electrolyte values, to represent three levels of hemoglobin values and to represent the visual appearance of hemolyzed blood.

These three formulations were as follows:

| | Acidosis (I) | Normal (II) | Alkalosis (III) |
|---|---|---|---|
| HEPES | 40.0 mM | 40.0 mM | 40.0 mM |
| NaOH | 20.0 | 25.7 | 29.6 |
| KCl | 3.0 | 5.0 | 7.0 |
| LiCl | 0.4 | 1.1 | 2.6 |
| NaCl | 73.2 | 81.5 | 99.3 |
| $CaCl_2$ | 3.5 | 2.5 | 1.7 |

|  | Acidosis (I) | Normal (II) | Alkalosis (III) |
|---|---|---|---|
| NaHCO$_3$ | 21.3 | 23.9 | 19.4 |
| Citric acid | 2.0 | 1.7 | 1.5 |

Three different levels of dyes were added to the corresponding buffer solutions.

|  | Acidosis (I) | Normal (II) | Alkalosis (III) |
|---|---|---|---|
| Red Dye #27 | 2.34 mM | 3.72 mM | 4.84 mM |
| Yellow Dye #23 | 1.57 | 2.6 | 3.39 |
| Blue Dye #9 | 0.016 | 0.04 | 0.08 |

The buffered dye solutions were then separately placed in a container which was thermally controlled to 25° C. The appropriate gas mixture was then bubbled through each solution at a rate of 5 to 7 L/min. until the pH, pCO$_2$ and pO$_2$ reached equilibrium values, as determined by appropriate blood gas analyzers. The gas mixtures used had the following compositions:

|  | Acidosis (I) | Normal (II) | Alkalosis (III) |
|---|---|---|---|
| CO$_2$ | 6.5% | 4.1% | 2.3% |
| O$_2$ | 5.9 | 11.8. | 18.0 |
| N$_2$ | 87.6 | 84.1 | 79.7 |

After equilibrium was reached, the gaseous solution was subdivided into 2.6 ml quantities and placed into 3 ml glass ampules which had been purged with the same gas mixture used in bringing the solution to equilibrium. The filled ampules were heat-sealed.

The control liquid had an appearance of a hemoglobin solution and showed the corresponding hemoglobin value equivalents as the following table:

|  | THb | O$_2$Hb % | O$_2$SAT % | COHb % | MetHb % | O$_2$Ct | Vol % O$_2$ |
|---|---|---|---|---|---|---|---|
| ACIDOSIS (I) |  |  |  |  |  |  |  |
| Corning 2500 | 9.0 g ± 0.5 g/ 100 ml |  | −43 ± 3 | 70 ± 5 | 63 ± 5 | −5.3 ± 0.3 |  |
| IL 282 | 5.5 ± 0.5 | −38 ± 3 |  | 112 ± 5 | 0.9 ± 0.2 |  | −2.9 ± 0.3 |
| Normal (II) |  |  |  |  |  |  |  |
| Corning 2500 | 14. ± 0.5 |  | −40 ± 3 | 65 ± 5 | 64 ± 5 | −7.5 ± 0.4 |  |
| IL 282 | 8.8 ± 0.5 | −35 ± 3 |  | 101 ± 5 | 6.9 ± 0.5 |  | −4.2 ± 0.3 |
| Alkalosis (III) |  |  |  |  |  |  |  |
| Corning 2500 | 18 ± 0.5 |  | −39 ± 3 | 64 ± 5 | 64 ± 5 | −9.4 ± 0.4 |  |
| IL 282 | 11.5 ± 0.5 | −32 ± 3 |  | 93 ± 5 | 11.9 ± 0.5 |  | −5.0 ± 0.3 |

The formulated liquid also had three levels of concentration of electrolytes as measured by the following different models of ion selective electrode instrumentation:

|  | Acidosis (I) | Normal (II) | Alkalosis (III) |
|---|---|---|---|
| Na |  |  |  |
| Corning 902 | 120 ± 3 mM | 140 ± 3 mM | 165 ± 4 mM |
| 614 | 120 ± 3 | 140 ± 3 | 165 ± 4 |
| Nova-1 | 120 ± 3 | 140 ± 3 | 160 ± 4 |
| IL-501 | 120 ± 3 | 140 ± 3 | 160 ± 4 |
| K |  |  |  |
| Corning 902 | 3.0 ± 0.3 mM | 5.0 ± 0.3 mM | 7.4 ± 0.4 mM |
| 614 | 3.0 ± 0.3 | 5.0 ± 0.3 | 7.4 ± 0.4 |
| Nova-1 | 3.0 ± 0.3 | 5.0 ± 0.3 | 7.0 ± 0.4 |
| IL-501 | 3.0 ± 0.3 | 5.0 ± 0.3 | 7.0 ± 0.4 |
| Total Ca Nova-7 | 3.5 ± 0.2 mM | 2.5 ± 0.2 mM | 1.7 ± 0.2 mM |
| Ionized Ca (Ca$^{++}$) Nova-7 | 1.6 ± 0.1 mM | 1.1 ± 0.1 mM | 0.6 ± 0.1 mM |
| Cl Nova-5 | 80 ± 1 mM | 100 ± 2 mM | 120 ± 3 mM |

The ampuled formulated liquid has the corresponding values of pH, pCO$_2$ and pO$_2$ for the blood gas analyzers.

|  | Acidosis (I) | Normal (II) | Alkalosis (III) |
|---|---|---|---|
| pH (unit) | 7.15 (7.10–7.20) | 7.4 (7.38–7.42) | 7.6 (7.58–7.62) |
| pCO$_2$ mmHg | 70 (66–72) | 40 (38–42) | 22 (20–24) |
| pO$_2$ mmHg | 60 (58–67) | 102 (100–104) | 150 (145–155) |

Those values were measured at 37° C.

The ampules containing formulated liquid can be heat sterilized at 15 PSI for 30 minutes for long term shelf life.

EXAMPLE 2

Control standards were produced having the compositions described previously as Formulation II. These control solutions were placed in containers which were thermally controlled to maintain a temperature of about 25° C. The appropriate gas mixture, as described in the previous example, was bubbled through each solution at a rate of about 5 to 7 L/min until the pH, the pCO$_2$ and the pO$_2$ reached equilibrium values as determined by appropriate blood gas analyzers.

After equilibrium was reached, the gaseous solution was subdivided into 1.7 ml samples and placed into 2 ml glass ampules purged with the same gas mixture used to bring the solution to equilibrium. The filled ampules were then sealed using a heat source.

The resulting liquid control standards were then suited for use as control standards in both pH/blood gas and electrolyte instrumentation.

Equivalents

Those skilled in the art will recognize, or be able to ascertain using no more than routine experimentation, many equivalents to the specific embodiments of the invention described herein. Such equivalents are intended to be encompassed by the following claims.

For example, it will be understood by one having ordinary skill in the art that other dye combinations can be used which can absorb light as hemoglobin does. This invention is not limited to the illustrated examples of dye combinations.

I claim:

1. An autoclavable, stable, homogeneous liquid control standard for blood analysis instrumentation systems comprising an aqueous solution containing a buffering agent in an amount sufficient to maintain the control standard pH in a range of from about 7.1 to about 7.7 and additionally containing sufficient bicarbonate ions to provide a $pCO_2$ from about 15 mmHg to about 80 mmHg, gaseous oxygen to provide a $pO_2$ of from about 50 mmHg to about 400 mmHg retained, a source of calcium to maintain a total calcium concentration in a predetermined range and a sequestering agent to form complexes with calcium to maintain an ionized calcium concentration in a predetermined range.

2. A control standard as in claim 1 wherein the ionized calcium concentration is in the range of about 0.5 mM to about 1.7 mM, and the total calcium concentration is in the range of about 1.3 mM to about 3.6 mM.

3. A control standard as in claim 2 wherein the ratio of ionized calcium concentration to total calcium concentration is in the range of about 30% to about 60%.

4. A control standard as in claim 1 which additionally contains salts of electrolytes other than calcium.

5. A control standard as in claim 4 wherein the control standard contains a predetermined concentration of ions selected from the group consisting of sodium ions, potassium ions, lithium ions and mixtures thereof.

6. A control standard as in claim 1 wherein the agent to form complexes with the ionized calcium is selected from the group consisting of alpha-amino acids, alpha-hydroxy acids, dicarboxylic acids, polycarboxylic acids and derivatives thereof.

7. A control standard as in claim 1 which additionally contains an absorbance means to provide a control test corresponding to a predetermined level of hemoglobin and hemoglobin fractions.

8. A control standard as in claim 7 wherein the agent to form complexes with the ionized calcium comprises citric acid.

9. A control standard as in claim 7 wherein the absorbance means comprises dyes selected from the group consisting of Acid Red Dye #27 (CI 16185), Acid Yellow Dye #23 (CI 19140), Acid Blue Dye #9 (CI 42090), Ponceau 3R Red Dye (CI 16155) and any combination thereof.

10. A control standard as in claim 1 wherein the pH ranges from about 7.10 to about 7.20, the $pCO_2$ ranges from about 60 mmHg to about 70 mmHg, the $pO_2$ ranges from about 50 mmHg to about 65 mmHg, the ionized calcium concentration ranges from about 1.5 mM to about 1.7 mM, the total calcium concentration ranges from about 3.3 mM to about 3.6 mM and the concentration ratio of ionized calcium to total calcium is in the range of about 30% to about 60%.

11. A control standard as in claim 10 additionally containing absorbance means to simulate blood having a low level of total hemoglobin.

12. A control standard as in claim 1 wherein the pH ranges from about 7.35 to about 7.45, the $pCO_2$ ranges from about 35 mmHg to about 45 mmHg, the $pO_2$ ranges from about 95 mmHg to about 110 mmHg, and the ionized calcium concentration is approximately 1.1 mM and the total calcium concentration is about 2.5 mM.

13. A control standard as in claim 12 additionally containing absorbance means to simulate blood having a normal level of total hemoglobin.

14. A control standard as in claim 1 wherein the pH ranges from about 7.55 to about 7.65, the $pCO_2$ ranges from about 15 mmHg to about 25 mmHg, the $pO_2$ ranges from about 140 mmHg to about 160 mmHg, the ionized calcium concentration is approximately 0.6 mM and the total calcium concentration is approximately 1.7 mM.

15. A control standard as in claim 14 additionally containing absorbance means to simulate blood having a high level of total hemoglobin.

16. An autoclavable, stable, homogeneous liquid control standard for blood analysis instrumentation systems comprising an aqueous solution containing a buffering agent in an amount sufficient to maintain the control standard pH in a range of from about 7.1 to about 7.7 and additionally containing sufficient bicarbonate ion to provide a $pCO_2$ ranging from about 50 mmHg to about 80 mmHg, gaseous oxygen to provide a $pO_2$ ranging from about 15 mmHg to about 400 mmHg retained, a calcium salt to provide a total calcium concentration in a range of between about 1.3 mM and about 3.6 mM, a citric acid calcium sequestering solution to provide an ionized calcium concentration ranging from about 0.5 mM to about 1.7 mM, wherein the concentration ratio of ionized calcium to total calcium is in a range of about 30% to about 60%, salts of sodium, potassium and lithium to provide an electrolyte concentration in the range of physiological sodium, potassium and lithium electrolyte concentration, and absorbance means corresponding to a predetermined level of hemoglobin and hemoglobin fractions, said absorbance means comprising dyes selected from the group consisting of Acid Red Dye #27 (CI 16185), Ponceau 3R Red Dye (CI 16155), Acid Yellow Dye #23 (CI 19140) and Acid Blue Dye #9 (CI 42090).

17. An autoclavable, stable, homogeneous liquid control standard for blood analysis instrumentation systems comprising an aqueous solution containing a buffering agent in an amount sufficient to maintain the control standard pH in a range of from about 7.1 to about 7.7 and additionally containing sufficient bicarbonate ion to provide a $pCO_2$ ranging from about 15 mmHg to about 80 mmHg, gaseous oxygen to provide a $pO_2$ ranging from about 50 mmHg to about 400 mmHg retained, a calcium salt to provide a total calcium concentration in a range of between about 1.3 mM and about 3.6 mM and an N-hydroxyethyliminodiacetic acid calcium sequestering solution to provide an ionized calcium concentration ranging from about 0.5 mM to about 1.7 mM, wherein the concentration ratio of ionized calcium to total calcium is in a range of about 30% to about 60%, and salts of sodium, potassium and lithium to provide an electrolyte concentration in the range of physiological sodium, potassium and lithium electrolyte concentration.

* * * * *